United States Patent
Wong et al.

(10) Patent No.: US 7,384,402 B2
(45) Date of Patent: Jun. 10, 2008

(54) EXPRESSION PAD

(75) Inventors: Daniel Wong, Sunnyvale, CA (US); Frank A. Chan, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 366 days.

(21) Appl. No.: 10/865,378

(22) Filed: Jun. 10, 2004

(65) Prior Publication Data

US 2005/0277972 A1    Dec. 15, 2005

(51) Int. Cl.
    *A61B 5/00*    (2006.01)
(52) U.S. Cl. ..................................... 600/583
(58) Field of Classification Search ............ 600/583, 600/573; 606/181–183, 185
    See application file for complete search history.

(56) References Cited

U.S. PATENT DOCUMENTS

| | | | |
|---|---|---|---|
| 3,623,475 A | | 11/1971 | Sanz |
| 3,626,929 A | * | 12/1971 | Sanz et al. ............. 600/583 |
| 4,924,879 A | * | 5/1990 | O'Brien ................. 600/583 |
| 6,063,039 A | * | 5/2000 | Cunningham et al. ..... 600/573 |
| 6,679,852 B1 | * | 1/2004 | Schmelzeisen-Redeker et al. ........ 600/583 |
| 2003/0191415 A1 | | 10/2003 | Moerman et al. |
| 2003/0195540 A1 | | 10/2003 | Moerman |

FOREIGN PATENT DOCUMENTS

| | | |
|---|---|---|
| DE | 10026170 A1 | 12/2001 |
| EP | 1 157 660 A1 | 11/2001 |
| JP | 09-313465 A1 | 12/1997 |
| WO | WO 01/89383 A2 | 11/2001 |
| WO | WO 01/95806 A2 | 12/2001 |
| WO | WO 02/078533 A2 | 10/2002 |
| WO | WO 2004/021886 A1 | 3/2004 |

* cited by examiner

*Primary Examiner*—Max Hindenburg
*Assistant Examiner*—Fangemonique Smith
(74) *Attorney, Agent, or Firm*—Woodard, Emhardt, Moriarty, McNett & Henry LLP

(57) ABSTRACT

An integrated body fluid sampling device is used to sample a body fluid from an incision in the skin of a body part. The device includes a lancet for forming the incision in the skin. A housing is coupled to the lancet. The housing defines at least in part a capillary channel with an opening. The capillary channel is sized to draw the body fluid from the incision via capillary action. An expression pad is coupled to the housing. The expression pad has opposing angled sides for compressing the backside of a body part where the incision is made. The lancet extends from the housing to form the incision. Fluid from the incision is drawn into the channel and is deposited on the test strip for analysis. A test strip is positioned along the capillary channel for analyzing the fluid.

11 Claims, 6 Drawing Sheets

EXPRESSION PAD

BACKGROUND

The present invention generally relates to integrated lancing test devices, and more specifically, but not exclusively, concerns a device and technique for expressing a body fluid.

The acquisition and testing of body fluids is useful for many purposes, and continues to grow in importance for use in medical diagnosis and treatment, and in other diverse applications. A common technique for collecting a body fluid sample is to form an incision in the skin to bring the fluid to the skin surface. A cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood.

An increase in blood flow to the fingertips allows a shallower incision, thus reducing the pain caused by the incision. While devices exist to increase blood flow to the sample sites, they generally do so by applying a tourniquet around the body part in which the incision is made. Because the devices wrap around the body part in close proximity to the location of the incision, these devices make it more difficult for the patient to view the incision site and testing operation. Thus, there is a need for improvement in this field.

SUMMARY

One aspect of the present invention concerns a device for expressing body fluid as part of a fluid sampling device that includes a housing with a lancet for creating an incision. The housing has a capillary channel for drawing body fluid from an incision that is created with the lancet. The pad has opposing angled surfaces for compressing a backside of a finger wherein the finger has a front side opposite the backside. The incision is formed in the front side of the finger.

Another aspect of the invention concerns a method of sampling a body fluid from an incision in the skin involving forming an incision in a front side of a finger. The finger has a backside that is opposite the front side. The backside is pressed against an expression device. The expression device has opposing angled surfaces that have a curved intersection. As the finger presses against the opposing angled surfaces, the angled surfaces compress the backside of the finger to force a body fluid out through the incision.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
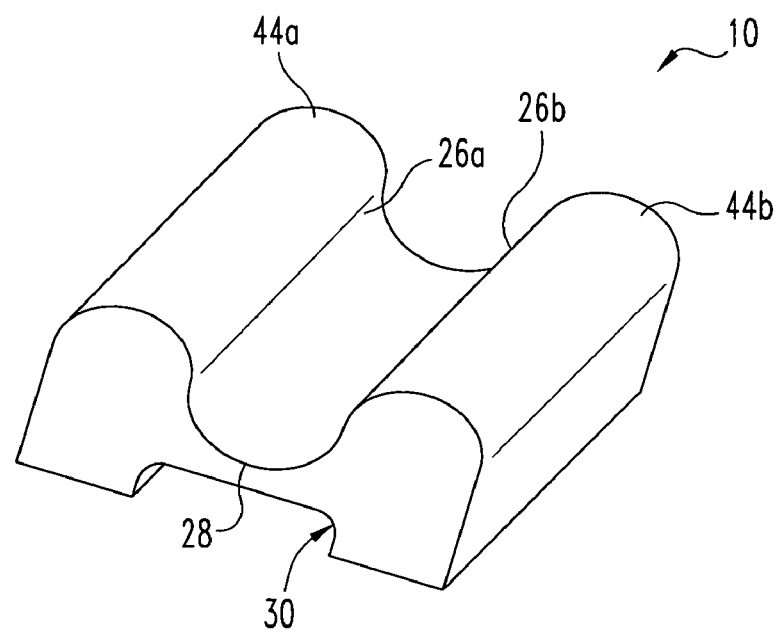
FIG. 1 is a perspective view of an expression pad according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and further applications of the principles of the invention as illustrated therein are contemplated as would normally occur to one skilled in the art to which the invention relates.

An integrated skin lancing device according to one embodiment of the present invention is configured to improve the quantity of blood produced at a sampling location. The device does this by compressing or pinching the skin surface on the backside of the finger pad in which the incision has either been made or will be made. For example, if the incision was made on the fingertip, the backside would include the fingernail and its surrounding skin. By compressing the backside of the finger, it was discovered that a greater volume of blood is produced at the incision in the fingertip. Compressing only the backside of a finger provides additional benefits. Because the pressure is applied to the opposite side of the incision, the incision is unobstructed. This allows the location of the incision to be determined more accurately and the body fluid sample acquired more easily.

Figure 2:
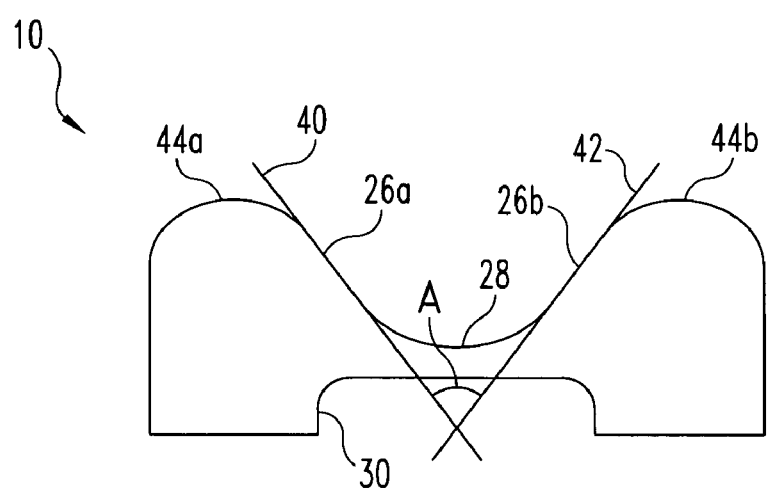
FIG. 2 is a front elevational view of the FIG. 1 expression pad.

An expression pad 10 according to one embodiment of the present invention will now be described with reference to FIGS. 1 and 2. In the illustrated embodiment, the expression pad 10 is made from compressible material such as foam rubber. The pad 10 defines a first skin contacting surface 26*a* and a second skin contacting surface 26*b*. As shown, the first skin contacting surface 26*a* and the second skin contacting surface 26*b* are angled with respect to one another. At the intersection between the skin contacting surfaces 26*a*, 26*b*, the pad 10 has a curved surface 28. The first skin contact surface 26*a* faces the second skin contacting surface 26*b*. The intersection of a plane 40 containing the first skin contacting surface 26*a* and a plane 42 containing the second skin contacting surface 26*b* forms an angle A. In one embodiment angle A is generally 120°.

The skin contacting surfaces 26*a*, 26*b* compress the backside of the finger when the finger is placed against the curved surface 28. The skin contacting surfaces 26*a*, 26*b* rotate inward to further compress the backside of the finger during deflection of curved surface 28. The pad 10 has rounded compression surfaces 44*a*, 44*b* that are located adjacent to each of the skin contact surfaces 26*a*, 26*b*, and are opposite the curved surface rounded compression surfaces 44*a*, 44*b*. The rounded compression surfaces 44*a*, 44*b* limit the height of the expression pad 10 to isolate the compressing or pinching to the backside of the finger. Additionally, the interior surfaces of the rounded compression surfaces 44*a*, 44*b* facilitate compressing the sides of the backside of the finger.

The pad 10 additionally defines a flex cavity 30 to facilitate the inward flexing of the skin contact surfaces 26*a*, 26*b*. The flex cavity 30 is disposed opposite the skin contacting surfaces 26*a* or 26*b*. The flex cavity 30 is disposed generally extends the length of the pad 10. The flex cavity 30 allows a greater deflection of pad 10 which causes a greater inward deflection of the skin contact surfaces 26a, 26b when a finger is pressed against curved intersection 28. The portion of the pad 10 along side the flex cavity 30 extends the length of the pad 10. It is also contemplated that the flex cavity 30 includes a less dense material than pad 10 for facilitating a greater deflection of the curved intersection 28.

Figure 3:
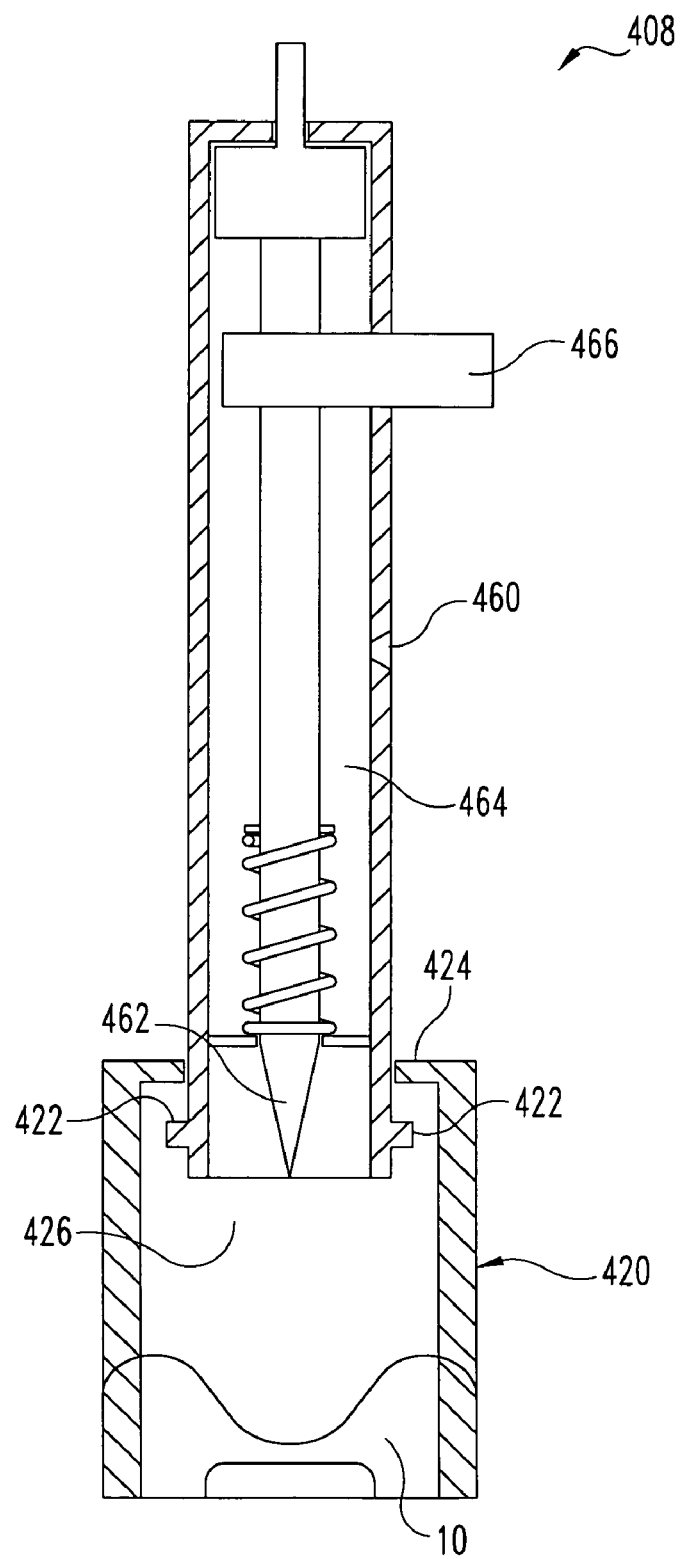
FIG. 3 is a perspective view of an integrated test device that incorporates the FIG. 1 apparatus.

As illustrated in FIG. 3, an integrated testing device 408 according to one embodiment includes the expression pad 10. The integrated test device 408 includes a housing 460 for containing the components of the device, a lancet 462 for creating the incision, an annular space 464 for drawing and collecting the body fluid from the incision, and a test trip 466 for testing or analyzing the body fluid. For the sake of brevity, a detailed description of all of the features of the device will not be provided. Rather, please refer to U.S. patent application Ser. No. 10/054,270, filed Jan. 22, 2002, Publication No. 2002/0103499, published Aug. 1, 2002 which is incorporated herein by reference in its entirety. As depicted, the expression pad 10 is placed in a support frame 420 movably attached to the housing 460. The support frame 420 at least partially encloses the pad 10. The support frame 420 is aligned with the lancet 462.

The support frame 420 defines finger access opening 426 to allow a finger to be placed in the expression pad 10 against the skin contacting surfaces 26a, 26b. The support frame 420 has a retention lip 424 that is adjacent to the housing 460 of the integrated test device 408. Barbs 422 attached to and extending from the housing 460 prevent the retention lip 424 from moving pass the barbs 422, and thus prevent the support frame 420 from separating from the housing 460. When the barbs 422 are in contact with the retention lip 424, the gap between the integrated test device 408 and the expression pad 10 is large enough so that the finger will pass through the finger access opening 426 to be placed into the expression pad 10. The adjustability of the gap allows the integrated test device 408 to be used on different finger sizes.

Additionally, the housing 460 is placed against the finger pad to determine precisely where the incision will result. To change the location of the incision, the housing 460 is moved away from the expression pad 10, the finger is repositioned in the expression pad 10 such that the desired location of the incision is aligned with the lancet 462, and the housing 460 is moved toward the finger pad in the expression pad 10. If necessary, this procedure is repeated until the lancet 462 is aligned with the desired location for the incision.

It is also contemplated that the expression pad 10 can be positioned at a fixed distance from the housing 460. In this embodiment, the housing 460 is close enough to the finger such that the body fluid exiting the incision collects in the surface of the finger and extends toward the housing 460 and is transferred into the capillary channel 464 of the integrated test device 408. Alternatively, the lancet 462 can be extended toward the body fluid that has collected on the finger so as to draw the body fluid into the capillary channel 464.

Figure 4:
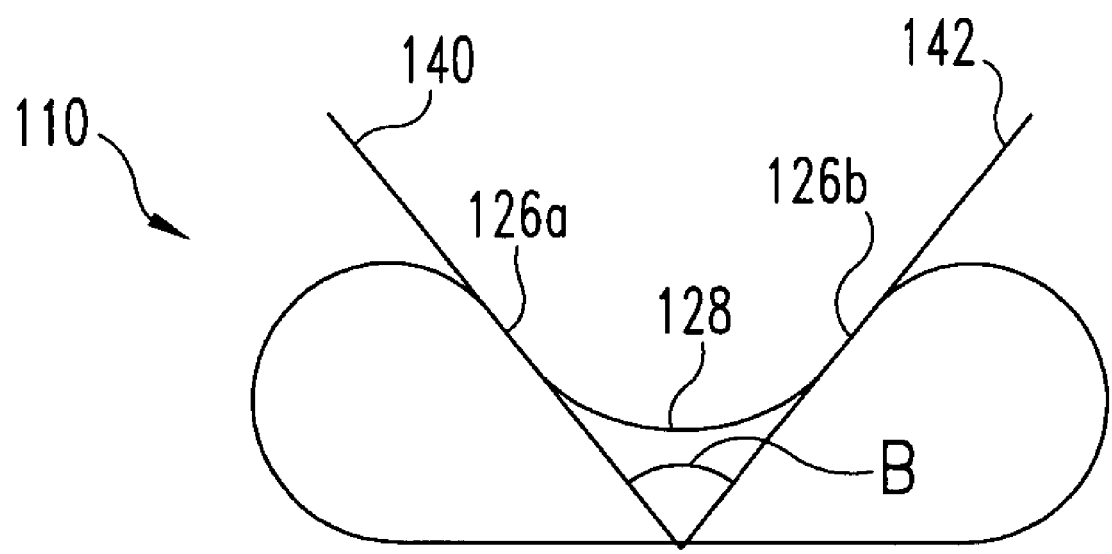
FIG. 4 is a front elevational view of an expression pad according to another embodiment.

FIG. 4 illustrates an expression pad 110 according to another embodiment which generally results in a larger average volume of body fluid during expressing. As illustrated, the expression pad 110 includes a first skin contacting surface 126a and a second skin contacting surface 126b. At the intersection between the skin contacting surfaces 126a, 126b, the pad 110 has a curved surface 128. The first skin contacting surface 126a faces the second skin contacting surface 126b. The intersection of the plane 140 containing the first skin contacting surface 126a and the plane 142 containing the second contacting surface 126b forms an angle, B. In one embodiment, B is generally 90°. The skin contacting surfaces 126a, 126b compress the backside of the finger when the backside of the finger is placed against the curved surface 128. The skin contacting surfaces 26a, 26b rotate inward to further compress the backside of the finger during deflection of curved surface 28. The pad 124 has a solid underside. It is also contemplated that the expression pad 110 be incorporated into an integrated test device similar to the one shown in FIG. 3.

Figure 5A:
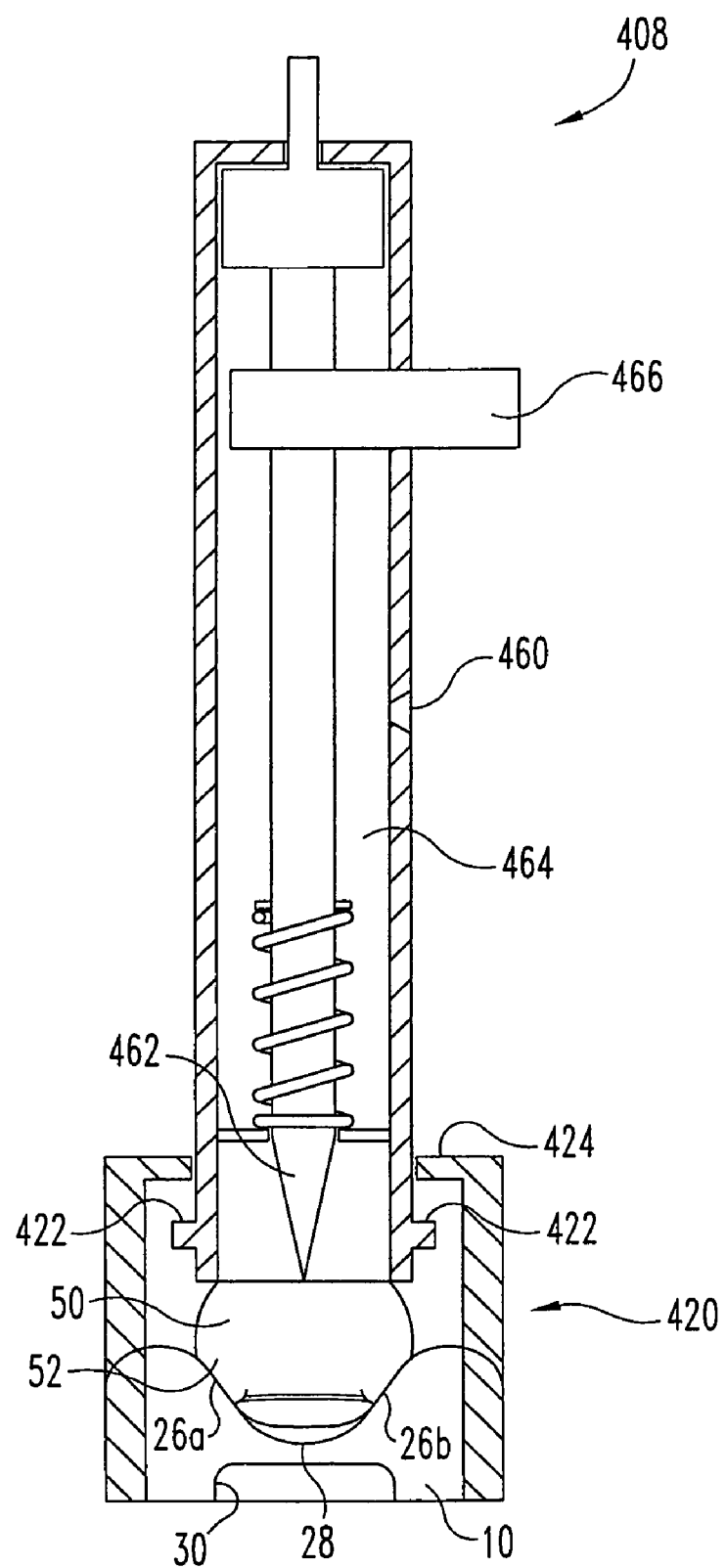
FIGS. 5A, 5B, and 5C are cut-away side views of the FIG. 1 expression pad in positions during use.
Figure 5B:
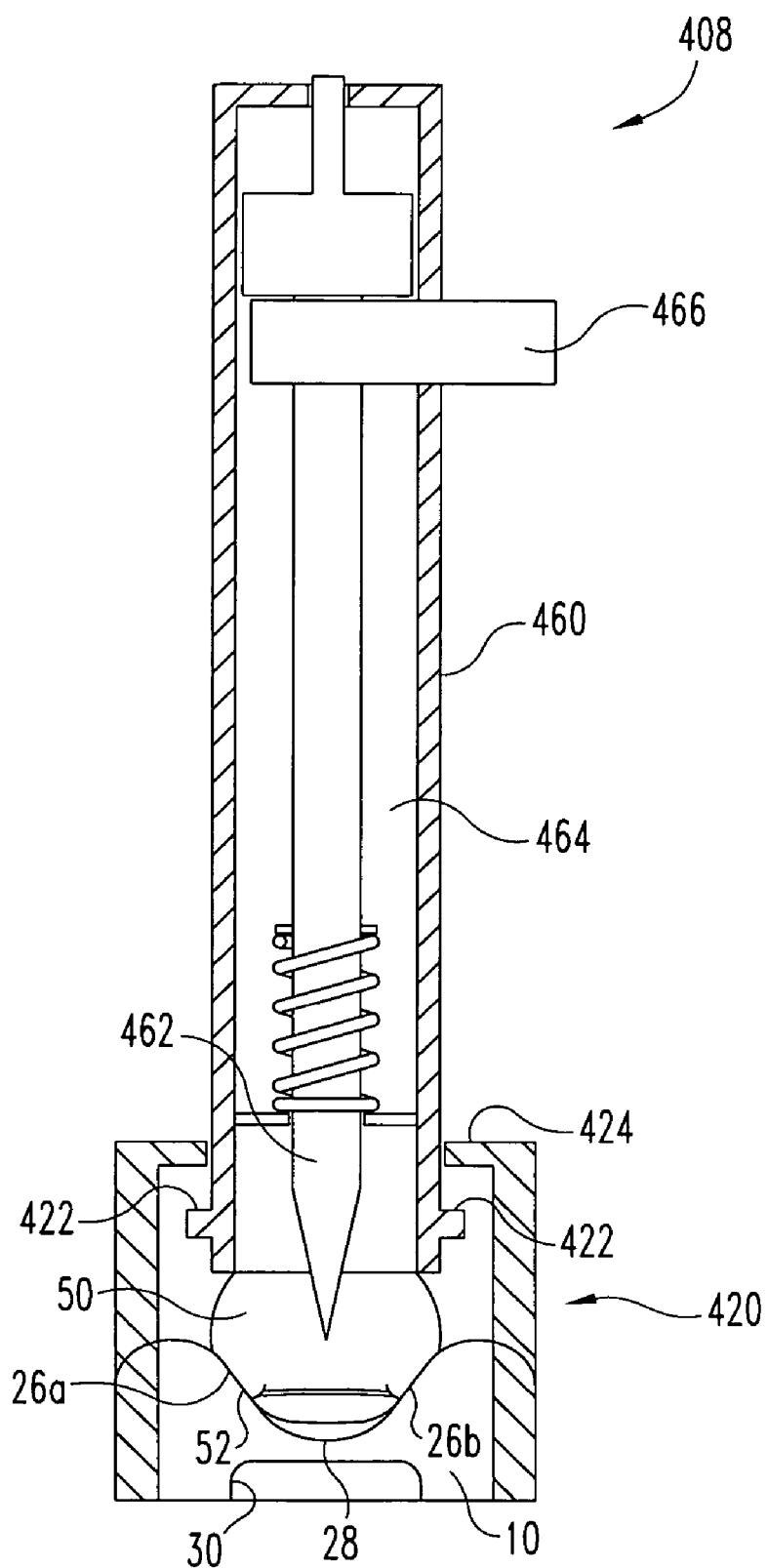
Figure 5C:
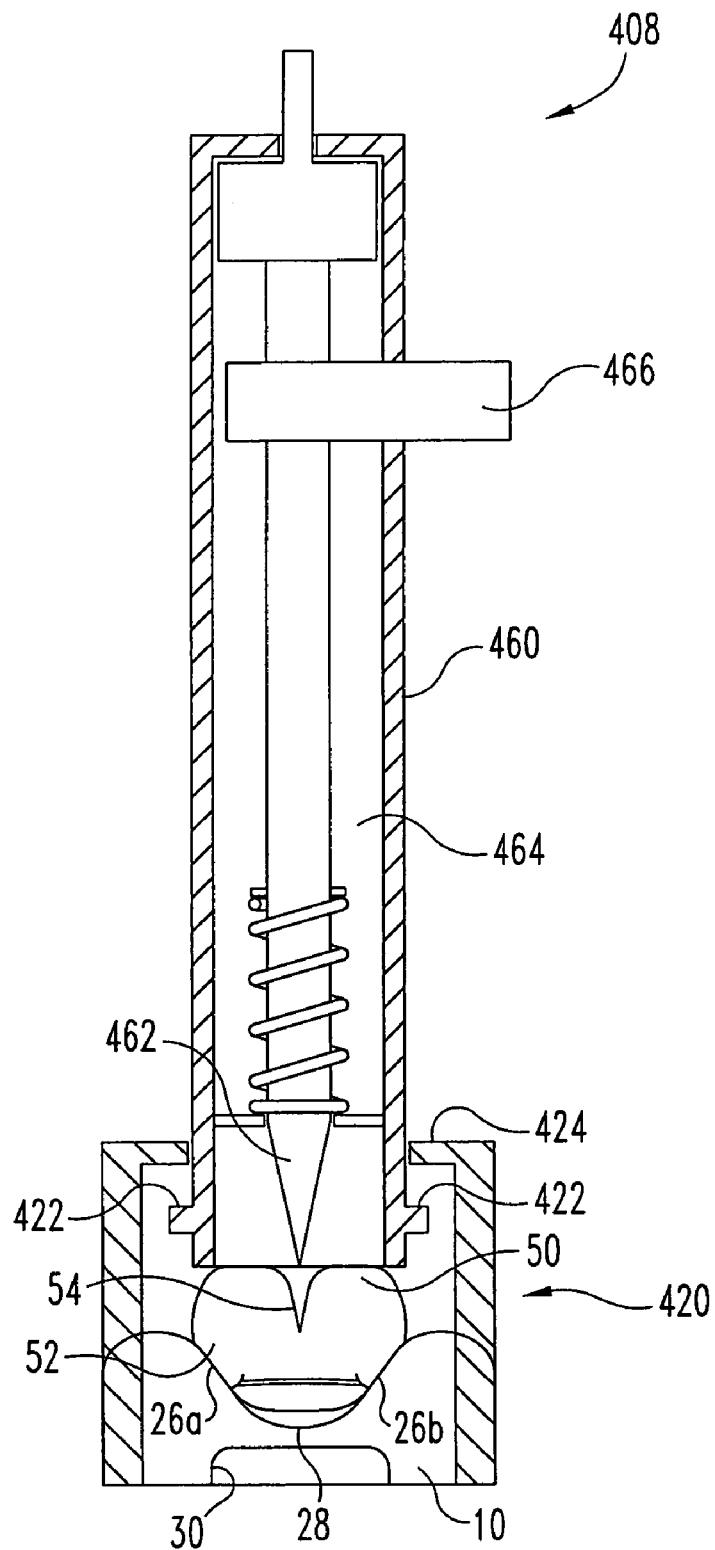

A technique for sampling body fluid with the sampling device of FIG. 3 will now be described with reference to FIGS. 5A, 5B, and 5C. A finger is placed through the finger access opening 426 and into the expression pad 10 such that the finger pad 50 faces away from the expression pad 10 and toward the integrated test device 408. The backside of the finger 52 contacts first skin contacting surface 26a and second skin contacting surface 26b. The skin contacting surfaces 26a, 26b conform to and compress the backside of the finger 52. The backside of the finger 52 is pressed into the curved intersection 28 which causes the skin contacting surfaces 26a, 26b to pivot inward to further compress the backside of the finger 52. An incision 54 is then made into the finger pad 50. An increased volume of body fluid is forced through the incision as a result of the pressure exerted on the backside of the finger 52.

Alternatively, the expression pad 10 is separate and distinct from the integrated test device; thus, eliminating the support frame 420 between the housing 460 and the expression pad 10. The incision point is more visible because the support frame 420 does not partially enclose the expression pad 10. Additionally, because lancet 462 is not constrained to a particular alignment with expression pad 10, the incision location can be changed by only moving the integrated test device. The finger does not have to be repositioned in the pad 10. It is also contemplated that the finger pad 50 is lanced before being placed in the expression pad 10.

The technique for sampling fluid with an expression pad 10 separate and distinct from an integrated test device will now be described. The procedure is similar to the one described above with reference to FIGS. 5A, 5B, and 5C. The backside of the finger 52 is placed into the expression pad 10 such that the backside of the finger 52 contacts the skin contacting surfaces 26a, 26b and the curved surface 28. The skin contacting surfaces 26a, 26b conform to and compress the backside of the finger 52. The backside of the finger 52 is pressed into the curved intersection 28 which causes the skin contacting surfaces 26a, 26b to pivot inward to further compress the backside of the finger 52. The inward rotation of the skin contacting surfaces 26a, 26b causes the rounded contacting surfaces 44a, 44b to flex inward to contact and compress the backside of the finger 52. As the pad 10 bows and extends into the flex cavity 30, the skin contacting surfaces 26a, 26b and rounded compression surfaces 44a, 44b, further rotate inward to apply greater pressure to the backside of the finger 52. The integrated test device is positioned with the lancet 462 aligned with the desired incision location. An incision 54 is made in the finger 50. Alternatively, because the lancet 462 is separate from the expression pad 10, the incision can be made in the finger pad before the backside of the finger is placed into the expression pad 10.

While the invention has been illustrated and described in detail in the drawings and foregoing description, the same is to be considered as illustrative and not restrictive in character, it being understood that only the particular embodiment have been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A body fluid sampling device comprising:
   a housing defining a capillary channel with an opening configured to draw a body fluid via capillary action;
   a lancet for forming an incision in a front side of a finger, the finger has a backside that is opposite the front side, the lancet being slidably disposed within the housing; and
   a pad secured to the housing, and aligned with the lancet such that the slidable motion of the lancet is in the direction of the pad, the pad having a first angled surface interconnected to an opposing second angled surface wherein deflection of the interconnection causes the first surface to deflect toward the second surface to compress only the backside of the finger to express the body fluid from the incision without compressing the front side of the finger.

2. The body fluid sampling device of claim 1, further comprising a test area positioned along the capillary channel for analyzing the body fluid.

3. The body fluid sampling device of claim 1, further comprising a testing system positioned along the capillary channel to analyze the body fluid.

4. The body fluid sampling device of claim 1, wherein the pad defines a flex recess for facilitating the rotation of the opposing angled surfaces inward against the backside of the finger,
   the flex recess is opposite the opposing angled surfaces.

5. The body fluid sampling device of claim 1, wherein the pad is made of a compressible material.

6. The body fluid sampling device of claim 1, wherein the pad is made of foam rubber.

7. The body fluid sampling device of claim 1, wherein the opposing angled surfaces are oriented generally 90° to 120° apart.

8. A method for expressing a body fluid, comprising:
   providing an integrated device that includes a lancet, a housing, and an expression pad, wherein the lancet and the housing define an annular space for drawing body fluid via capillary action, wherein the expression pad is coupled to the housing to define a finger access opening, wherein the expression pad has opposing angled surfaces facing the lancet, wherein a finger has a backside with a fingernail and an opposite front side;
   inserting the finger into the finger access opening of the integrated device with the backside of the finger facing the expression pad and the front side of the finger facing the lancet;
   forming an incision in the front side of the finger; expressing the body fluid from the incision by pressing only the backside of the finger against the opposing angled surfaces of the expression pad without compressing the front side of the finger; and
   drawing the body fluid into the annular passage; and
   expressing the body fluid from the incision by pressing only the backside of the finger against the opposing angled surfaces of the expression pad without compressing the front side of the finger; and
   drawing the body fluid into the annular passage.

9. The method of claim 8, further comprising:
   drawing the body fluid into the annular space of the integrated device, wherein the integrated device includes a test strip; and
   analyzing the body fluid with the test strip.

10. The method of claim 8, wherein the expressing and the drawing occur simultaneously.

11. The method of claim 8, wherein said pressing occurs before said forming the incision.

* * * * *